United States Patent [19]

Yamamoto et al.

[11] 4,245,118
[45] Jan. 13, 1981

[54] OXIDATION OF UNSATURATED ALDEHYDES

[75] Inventors: Haruhisa Yamamoto; Kiyomori Ooura; Shinichi Akiyama, all of Takaoka, Japan

[73] Assignee: Nippon Zeon Co., Ltd., Tokyo, Japan

[21] Appl. No.: 1,783

[22] Filed: Jan. 8, 1979

[30] Foreign Application Priority Data

Jan. 17, 1978 [JP] Japan ................................. 53-3581

[51] Int. Cl.$^3$ ..................... C07C 51/25; C07C 57/055
[52] U.S. Cl. ..................... 562/532; 252/435; 252/437; 562/535; 562/546; 562/548; 568/400; 568/476
[58] Field of Search ............... 562/532, 535; 252/435, 252/437

[56] References Cited

U.S. PATENT DOCUMENTS

| | | | |
|---|---|---|---|
| 3,567,772 | 3/1971 | Yanagita et al. | 562/535 |
| 3,875,220 | 4/1975 | White et al. | 562/535 |
| 3,882,047 | 5/1975 | Niina et al. | 252/435 |
| 3,976,688 | 8/1976 | Akiyama et al. | 562/535 |
| 3,998,877 | 12/1976 | Oda et al. | 562/535 |
| 4,072,708 | 2/1978 | White et al. | 562/535 |
| 4,075,244 | 2/1978 | Akiyama et al. | 562/535 |
| 4,113,770 | 9/1978 | Akiyama et al. | 562/535 |
| 4,157,987 | 6/1979 | Dolhyj et al. | 562/535 |

FOREIGN PATENT DOCUMENTS

50-70318  6/1975  Japan .
50-83322  7/1975  Japan .
53-41653  11/1978  Japan .

*Primary Examiner*—Vivian Garner
*Attorney, Agent, or Firm*—Wenderoth, Lind & Ponack

[57] ABSTRACT

Catalysts for the oxidation of unsaturated aldehydes, said catalysts being expressed by the formula $$A_a B_b C_c Mo_d P_e O_f$$

wherein A represents at least one element selected from K, Rb, Cs and Tl; B represents at least one element selected from Be, Ag, Y, La, Nd, Sm and Hf; C represents at least one element selected from V, Cr, Ba, Sr, Al, Sn, Pb, Mn, Zr, W and Bi; a, b, c, d, e and f are the number of the atoms of A, B, C, Mo, P and O, respectively; and when d is 12, a, b and e are independently 0.05 to 12, c is 0 to 12, and f is the number of oxygen atoms which satisfies the valences of the other elements.

6 Claims, No Drawings

OXIDATION OF UNSATURATED ALDEHYDES

This invention relates to novel catalysts for oxidation of unsaturated aldehydes, and a process for preparing unsaturated carboxylic acids with the use of said catalysts. More specifically, the invention concerns a process which comprises catalytically oxidizing unsaturated aldehydes in the vapor phase in the presence of a catalyst having superior catalytic activity and undergoing no reduction in activity by impurities such as olefins, thereby to prepare the corresponding unsaturated carboxylic acids.

In recent years, extensive studies have been made on a process which comprises catalytically oxidizing olefins such as propylene or isobutylene, or tert-butyl alcohol in the vapor phase using molecular oxygen to prepare the corresponding unsaturated aldehydes such as acrolein or methacrolein (hereinafter referred to as first stage oxidation; catalysts to be used in this reaction are called first stage oxidation catalysts), and a process which comprises further catalytically oxidizing these unsaturated aldehydes in the vapor phase using molecular oxygen to prepare the corresponding unsaturated carboxylic acids such as acrylic acid or methacrylic acid (hereinafter referred to as second stage oxidation; catalysts for use in this reaction are called second stage oxidation catalysts). As a result, a number of first stage oxidation catalysts and second stage oxidation catalysts have already been proposed. Their catalytic activity, however, is still not entirely satisfactory, and a desire has been raised for the development of catalysts, especially second stage oxidation catalysts, which have better performances.

In the production of unsaturated carboxylic acids, a process involving the second stage oxidation using unsaturated aldehydes in the purified form and a process comprising the second stage oxidation of the reaction mixture obtained by the first stage oxidation without purifying the reaction mixture (hereinafter called the first stage-second stage continuous method) are both known. Since the latter process does not need such treating steps as the separation and purification of unsaturated aldehydes, it is advantageous in apparatus, operation and economy and is considered commercially advantageous as well. However, if the first stage-second stage continuous method is performed using known first stage oxidation catalysts and second stage oxidation catalysts, then the catalytic activity of the second stage oxidation catalysts (conversion of unsaturated aldehydes, and yield and selectivity of unsaturated carboxylic acids) is generally much inferior to that exhibited if the second stage oxidation alone is carried out under the same reaction conditions using purified unsaturated aldehydes. This tendency is conspicuous particularly in the production of methacrylic acid from isobutylene. This phenomenon is known to be caused by small amounts of tarry substances formed as by-products in the first stage oxidation, or small amounts of unsaturated hydrocarbons such as the unreacted isobutylene. Particularly the unsaturated hydrocarbons are known to cause the phenomenon.

No proposals, therefore, have yet been offered to enable methacrylic acid to be produced on a commercial scale by the first stage-second stage continuous method. To make such method feasible, it would be insufficient simply to increase the catalytic activity in the second stage oxidation, and it is required to develop novel second stage oxidation catalysts which do not deteriorate even in the presence of small amounts of by-products or the unreacted isobutylene contained in the first stage oxidation reaction mixture.

The object of the present invention is therefore to provide novel second stage oxidation catalysts which are free from the above-described drawbacks of so far known catalysts for oxidation of methacrolein, which have excellent catalytic activity and which undergo little deterioration by olefins, etc.

We have eagerly made studies and found that catalysts expressed by the general fromula [I] shown below are very useful in attaining said object, and that the catalysts are also suitable for oxidation of other unsaturated aldehydes such as acrolein.

Thus, the present invention provides catalysts for oxidation of unsaturated aldehydes, said catalysts being expressed by the general formula [I]

$$A_aB_bC_cMo_dP_eO_f \qquad [I]$$

wherein A represents at least one element selected from K, Rb, Cs and Tl; B represents at least one element selected from Be, Ag, Y, La, Nd, Sm and Hf; C represents at least one element selected from V, Cr, Ba, Sr, Al, Sn, Pb, Mn, Zr, W and Bi; a, b, c, d, e and f are the number of the atoms of A, B, C, Mo, P and O, respectively; and when d is 12, a, b, and e independently denote 0.05 to 12, c denotes 0 to 12, and f denotes the number of oxygen atoms which satisfies the valences of the other elements.

Of the above catalysts, particularly preferred are those in which when d is 12, a, b, c and e are independently 0.1 to 8 and f is the number of oxygen atoms which satisfies the valences of the other elements. Also particularly preferred are those in which component B is Be, Y, La or Nd and in which component C is V, Cr, Ba, Sr, Mn or Zr.

The feature of the catalysts of the present invention is that they contain component B. Since component B is contained in the catalyst, the use of the catalyst of the prevent invention enables unsaturated carboxylic acids to be obtained from unsaturated aldehydes in high yields at high selectivities by a stable reaction under practical reaction conditions. Moreover, even if small amounts of unsaturated hydrocarbons are present in the starting gas containing methacrolein, reduction of the catalytic activity hardly occurs. As a result, it becomes possible to produce methacrylic acid by the first stage-second stage continuous method though such production has been considered impossible when using known catalysts. Further, the conventional catalysts have often had difficulty in reproducing their catalytic activity, while the catalysts of the present invention always exhibit good activity.

The catalysts for use in the process of the present invention can be prepared by the so-called evaporation to dryness method, coprecipitation method, etc. which are known in the art. The starting materials used in preparing the catalysts are, for example, salts such as ammonium salts, nitrates, and halides; free acids; acid anhydrides; poly-acids; oxides; heteropolyacids containing molybdenum such as phosphomolybdic acid; and heteropoly-acid salts such as acid salts, ammonium salts and alkali metal salts of heteropoly-acids. Particularly preferred is the use as the starting materials of compounds such as heteropoly-acids or their acid salts, ammonium salts and alkali metal salts which are capable of forming complex compounds.

The so prepared catalyst composition is calcined at a temperature of 250° to 700° C., preferably 300° to 550° C. for several hours to several tens of hours in air, a reducing atmosphere or the starting gas before it is used as a catalyst.

The state in which the respective elements exhibiting catalytic action, including oxygen, are present in the catalyst of the present invention is not entirely clear, but is is believed that these elements are not in the form of a mere mixture of their oxides.

The catalyst of the present invention can be used as it is, but can also be used as deposited on a carrier of a suitable shape or as diluted with a carrier (diluent) in the form of a powder, sol or gel. The carrier may be any known carrier, examples of which include titanium dioxide, silica gel, silica sol, diatomaceous earth, silicon carbide, alumina, pumice, silica-alumina, bentonite, zirconia, graphite, refractories, and zeolite.

The starting unsaturated aldehydes for use in the process of the present invention are preferably acrolein and methacrolein. When the first stage-second stage continuous method is employed, it is preferred to use as the starting material the reaction mixture obtained by the first stage oxidation of propylene, isobutylene or tert-butyl alcohol. As a source of molecular oxygen, oxygen can be used alone, but industrially, air is suitable for practical purposes, and if the first stage-second stage continuous method is employed, it is also possible to utilize the unreacted oxygen contained in the reaction mixture of the first stage oxidation.

A gas exerting no influence on the reaction, such as steam, nitrogen, carbon dioxide, helium, argon, or saturated hydrocarbon (e.g. methane, ethane, propane, butane, pentane, etc.) may be introduced as a diluent to the reaction system. Further, when the first stage-second stage continuous method is employed, the inclusion of the unreacted starting material (propylene, isobutylene, tert-butyl alcohol, oxygen, etc.), diluent, by-products and so forth that are contained in the reaction mixture of the first stage oxidation would substantially exercise no adverse influences on the reaction.

The concentration of the unsaturated aldehyde in the starting mixture is preferably in the range of 1 to 25% by volume. The ratio of the unsaturated aldehyde to oxygen is 1:0.1 to 25.0, preferably 1:0.1 to 20.0. The reaction temperature is 300° to 500° C., preferably, 330° to 450° C. The contact time (based on 0° C., 1 atmosphere) is 0.1 to 20 seconds, preferably, 0.5 to 15 seconds.

In the present invention, the reaction pressure is not a particularly important factor, and high pressures would be usable, but a pressure of about 1 to 10 atmospheres is suitable for practical use. The reaction apparatus can adopt a fixed bed, fluidized bed or moving bed, and the reaction product can be separated and purified by a known ordinary method.

The present invention will be described more concretely below with reference to examples, in which the conversion of the unsaturated aldehyde, and the yield and selectivity of the unsaturated carboxylic acid are defined as follows, the analyses having been all made by a gas chromatograph:

$$\text{Conversion (\%)} = \frac{\text{Unsaturated aldehyde reacted (mol)}}{\text{Unsaturated aldehyde supplied (mol)}} \times 100$$

$$\text{Yield (\%)} = \frac{\text{Unsaturated carboxylic acid formed (mol)}}{\text{Unsaturated aldehyde supplied (mol)}} \times 100$$

$$\text{Selectivity (\%)} = \frac{\text{Yield}}{\text{Conversion}} \times 100$$

In the catalysts shown in the examples, the indication of oxygen is omitted for simplification.

EXAMPLE 1

Ammonium molybdate (212 g) was dissolved, with heating, in 300 ml of water. To this aqueous solution were added an aqueous solution of 23 g of 851% phosphoric acid dissolved in 50 ml of water and an aqueous solution of 20.2 g of potassium nitrate dissolved, with heating, in 200 ml of water, and then the mixture was stirred. To the resulting aqueous solution was added 2.5 g of finely divided beryllium oxide which had been obtained by destroying beryllium nitrate in a stream of air at 500° C. for 16 hours. While being vigorously stirred, they were evaporated to dryness. The resulting product was calcined for 16 hours in a muffle furnace held at 450° C., and it was then pulverized, and sifted to a size of 4 to 8 mesh. The resultant product had the composition $Mo_{12}P_2Be_1K_2$ [catalyst No. (1) in Table 1—1].

In the same way, catalysts No. (2) to No. (4) in Table 1—1 were prepared, except that 29.5 g of rubidium nitrate, 39.0 g of cesium nitrate and 53.3 g of thallium nitrate were each used instead of the potassium nitrate. Similarly, catalysts No. (5) to No. (16) in Table 1—1 were prepared, except that 11.6 g of silver oxide, 11.3 g of yttrium oxide, 8.2 of lanthanum oxide, 8.4 g of neodymium oxide, 18.7 g of samarium oxide and 21.0 g of hafnium oxide, all in the form of a fine powder, were each used instead of the beryllium oxide.

Furthermore, the above-described procedure was repeated, without the use of some of the starting compounds, to prepare control catalysts No. (C-1) to No. (C-15) shown in Table 1-2.

Next, 10.0 ml of the catalyst was charged into a stainless steel reaction tube having an inside diameter of 2.5 cm and a length of 60 cm, followed by heating to 350° C. over a metal bath. A feed gas consisting of methacrolein:$O_2$:$N_2$:$H_2O$=1:1.5:17.5:10 (molar ratio) was passed through the catalyst layer for a residence time of 1.8 seconds (based on 0° C., 1 atmosphere) to carry out the reaction. The results are tabulated in Tables 1—1 and 1-2. The purity of the methacrolein used was 99.5% by weight.

TABLE 1-1

| Catalyst No. | Composition of catalyst (atomic ratio) | Conversion of methacrolein (%) | Per-pass yield (selectivity) of methacrylic acid (%) |
|---|---|---|---|
| Present Invention | | | |
| (1) | $Mo_{12}P_2Be_1K_2$ | 66.4 | 47.3 (71.2) |
| (2) | $Mo_{12}P_2Be_1Rb_2$ | 70.5 | 50.9 (72.2) |
| (3) | $Mo_{12}P_2Be_1Cs_2$ | 73.0 | 52.6 (72.1) |
| (4) | $Mo_{12}P_2Be_1Tl_2$ | 71.6 | 51.3 (71.6) |
| (5) | $Mo_{12}P_2Ag_1Rb_2$ | 69.5 | 48.0 (69.1) |
| (6) | $Mo_{12}P_2Ag_1Cs_2$ | 73.9 | 50.7 (68.6) |
| (7) | $Mo_{12}P_2Y_1Tl_2$ | 74.8 | 52.3 (69.9) |
| (8) | $Mo_{12}P_2Y_1K_2$ | 68.7 | 46.8 (68.1) |

TABLE 1-1-continued

| Catalyst No. | Composition of catalyst (atomic ratio) | Conversion of methacrolein (%) | Per-pass yield (selectivity) of methacrylic acid (%) |
|---|---|---|---|
| (9) | $Mo_{12}P_2La_{0.5}Rb_2$ | 75.5 | 51.7 (68.5) |
| (10) | $Mo_{12}P_2La_{0.5}Tl_2$ | 79.2 | 53.4 (67.4) |
| (11) | $Mo_{12}P_2Nd_{0.5}K_2$ | 69.3 | 45.5 (65.7) |
| (12) | $Mo_{12}P_2Nd_{0.5}Cs_2$ | 74.7 | 49.0 (65.6) |
| (13) | $Mo_{12}P_2Sm_{0.5}Tl_2$ | 66.3 | 44.7 (67.4) |
| (14) | $Mo_{12}P_2Sm_{0.5}Cs_2$ | 72.7 | 48.4 (66.6) |
| (15) | $Mo_{12}P_2Hf_1K_2$ | 70.2 | 48.1 (68.5) |
| (16) | $Mo_{12}P_2Hf_1Rb_2$ | 74.3 | 51.3 (69.0) |

TABLE 1-2

| Catalyst No. | Composition of catalyst (atomic ratio) | Conversion of methacrolein (%) | Per-pass yield (selectivity) of methacrylic acid (%) |
|---|---|---|---|
| Control | | | |
| (C-1) | $Mo_{12}P_2K_2$ | 39.7 | 18.6 (46.9) |
| (C-2) | $Mo_{12}P_2Rb_2$ | 40.0 | 22.9 (57.3) |
| (C-3) | $Mo_{12}P_2Cs_2$ | 44.9 | 27.8 (61.9) |
| (C-4) | $Mo_{12}P_2Tl_2$ | 39.6 | 25.2 (63.7) |
| (C-5) | $Mo_{12}P_2Be_1$ | 32.5 | 8.6 (26.5) |
| (C-6) | $Mo_{12}P_2Ag_1$ | 40.1 | 3.0 (7.5) |
| (C-7) | $Mo_{12}P_2Y_1$ | 27.6 | 3.7 (13.4) |
| (C-8) | $Mo_{12}P_2La_{0.5}$ | 55.8 | 2.0 (3.6) |
| (C-9) | $Mo_{12}P_2Nd_{0.5}$ | 57.3 | 2.5 (4.4) |
| (C-10) | $Mo_{12}P_2Sm_{0.5}$ | 55.5 | 1.5 (2.7) |
| (C-11) | $Mo_{12}P_2Hf_1$ | 21.0 | 4.2 (20.0) |
| (C-12) | $Mo_{12}Be_1Cs_2$ | 41.5 | 11.1 (26.7) |
| (C-13) | $Mo_{12}Y_1Rb_2$ | 41.5 | 7.6 (18.3) |
| (C-14) | $Mo_{12}La_{0.5}Tl_2$ | 48.3 | 7.0 (14.5) |
| (C-15) | $Mo_{12}Nd_{0.5}K_2$ | 47.6 | 7.5 (15.8) |

EXAMPLE 2

The catalysts shown in Table 2 were prepared in the same way as in Example 1, and the reaction was performed in the same manner as in Example 1. The results are illustrated in Table 2.

TABLE 2

| Catalyst No. | Composition of catalyst (atomic ratio) | Conversion of methacrolein (%) | Per-pass yield (selectivity) of methacrylic acid (%) |
|---|---|---|---|
| Present Invention | | | |
| (17) | $Mo_{12}P_1Be_1Rb_2$ | 68.9 | 49.5 (71.8) |
| (18) | $Mo_{12}P_2Be_3Cs_2$ | 68.1 | 48.7 (71.5) |
| (19) | $Mo_{12}P_3Ag_{0.5}K_4$ | 64.5 | 45.1 (69.9) |
| (20) | $Mo_{12}P_2Ag_4Cs_1$ | 72.6 | 49.6 (68.3) |
| (21) | $Mo_{12}P_1Y_1Tl_{0.5}$ | 73.9 | 51.4 (69.6) |
| (22) | $Mo_{12}P_2Y_{0.5}Cs_2$ | 74.2 | 52.0 (70.1) |
| (23) | $Mo_{12}P_2L_1Rb_3$ | 74.1 | 50.0 (67.5) |
| (24) | $Mo_{12}P_4La_2Cs_2$ | 75.6 | 52.4 (69.3) |
| (25) | $Mo_{12}P_2Nd_{0.5}K_{1.5}$ | 68.5 | 44.4 (64.8) |
| (26) | $Mo_{12}P_1Nd_{0.5}Rb_1$ | 70.5 | 45.8 (65.0) |
| (27) | $Mo_{12}P_2Sm_1Tl_2$ | 66.1 | 44.2 (66.9) |
| (28) | $Mo_{12}P_{0.5}Sm_{0.5}Cs_{1.5}$ | 68.6 | 46.0 (67.1) |
| (29) | $Mo_{12}P_1Hf_{0.5}K_4$ | 67.6 | 45.5 (67.3) |
| (30) | $Mo_{12}P_2Hf_2Rb_2$ | 74.4 | 50.4 (67.7) |
| (31) | $Mo_{12}P_2Be_1Y_{0.5}Cs_2$ | 76.1 | 53.6 (70.4) |
| (32) | $Mo_{12}P_1La_{0.5}K_{1.5}Cs_1$ | 80.4 | 54.8 (68.2) |
| (33) | $Mo_{12}P_2Be_1Hf_{0.5}Tl_2Cs_{0.5}$ | 76.7 | 54.1 (70.5) |

EXAMPLE 3

The catalysts numbered (34) to (50) in Table 3-1 were prepared in accordance with Example 1, with the exception of using additional starting compounds.

The additional starting compound used was an oxide obtained by decomposing ammonium metavanadate, chromium trioxide, ammonium paratungstate, tin dioxide or a nitrate of barium, strontium, aluminum, manganese, zirconium, lead or bismuth in a stream of air at 500° C. for 16 hours.

For comparison, control catalysts Nos. (C-16) to (C-26) were prepared by performing the same procedure as mentioned above, except that some of the starting compounds were not used.

Using the various catalysts thus prepared, the reaction was carried out in the same manner as in Example 1. The results obtained are tabulated in Table 3-1 and Table 3-2.

TABLE 3-1

| Catalyst No. | Composition of catalyst (atomic ratio) | Conversion of methacrolein (%) | Per-pass yield (selectivity) of methacrylic acid % |
|---|---|---|---|
| Present Invention | | | |
| (34) | $Mo_{12}P_2Be_1K_2V_{0.5}$ | 75.2 | 55.7 (74.1) |
| (35) | $Mo_{12}P_2La_{0.2}Cs_2V_1$ | 81.4 | 60.5 (74.3) |
| (36) | $Mo_{12}P_1Y_1Tl_2Cr_{1.5}$ | 75.2 | 52.2 (69.4) |
| (37) | $Mo_{12}P_2Nd_{0.5}Rb_2Cr_1$ | 76.4 | 52.8 (69.1) |
| (38) | $Mo_{12}P_2Be_{1.5}K_3Ba_{0.5}$ | 75.6 | 54.9 (72.6) |
| (39) | $Mo_{12}P_2Nd_{0.5}Cs_2Ba_1$ | 77.5 | 53.5 (69.0) |
| (40) | $Mo_{12}P_2Ag_2Tl_1Sr_3$ | 73.2 | 51.1 (69.8) |
| (41) | $Mo_{12}P_2Hf_{0.3}Rb_2Al_2$ | 77.5 | 53.6 (69.2) |
| (42) | $Mo_{12}P_2Sm_1Cs_2W_4$ | 73.0 | 50.0 (68.5) |
| (43) | $Mo_{12}P_1Be_{0.5}Cs_2Mn_1$ | 75.0 | 53.8 (71.7) |
| (44) | $Mo_{12}P_2Y_1Rb_2Mn_{0.5}$ | 76.8 | 54.3 (70.7) |
| (45) | $Mo_{12}P_2La_{0.2}Tl_2Zr_1$ | 81.4 | 55.5 (68.2) |
| (46) | $Mo_{12}P_1Nd_{0.2}Cs_2Zr_{0.5}$ | 77.9 | 51.7 (66.4) |
| (47) | $Mo_{12}P_2Be_{0.5}Cs_2Sn_{0.5}$ | 74.8 | 54.6 (73.0) |
| (48) | $Mo_{12}P_2Y_{0.5}Rb_2Pb_1$ | 78.0 | 55.4 (71.0) |
| (49) | $Mo_{12}P_2Hf_{0.5}K_2Bi_1$ | 74.0 | 51.4 (69.5) |
| (50) | $Mo_{12}P_2Sm_{0.5}Cs_2V_{0.2}Zr_{0.5}$ | 82.8 | 61.9 (74.8) |

TABLE 3-2

| Catalyst No. | Composition of catalyst (atomic ratio) | Conversion of methacrolein (%) | Per-pass yield (selectivity) of methacrylic acid (%) |
|---|---|---|---|
| Control | | | |
| (C-16) | $Mo_{12}P_2Cs_2V_1$ | 77.1 | 56.7 (73.5) |
| (C-17) | $Mo_{12}P_2Rb_2Cr_1$ | 71.3 | 46.1 (64.7) |
| (C-18) | $Mo_{12}P_2Cs_2Ba_1$ | 73.8 | 48.7 (66.0) |
| (C-19) | $Mo_{12}P_2Tl_1Sr_3$ | 56.4 | 28.9 (51.2) |
| (C-20) | $Mo_{12}P_2Rb_2Al_2$ | 69.5 | 43.0 (61.9) |
| (C-21) | $Mo_{12}P_2Cs_2W_4$ | 60.0 | 40.4 (67.3) |
| (C-22) | $Mo_{12}P_1Cs_2Mn_1$ | 68.7 | 46.0 (67.0) |
| (C-23) | $Mo_{12}P_2Tl_2Zr_1$ | 69.3 | 44.4 (64.1) |
| (C-24) | $Mo_{12}P_2Cs_2Sn_{0.5}$ | 53.8 | 30.9 (57.4) |
| (C-25) | $Mo_{12}P_2Rb_2Pb_1$ | 52.3 | 36.8 (70.4) |
| (C-26) | $Mo_{12}P_2K_2Bi_1$ | 61.6 | 40.2 (65.3) |

EXAMPLE 4

100 ml of each of the catalysts of the present invention and the control catalysts used in Examples 1 and 3 [catalysts Nos. (1), (5), (7), (9), (12), (35), (37), (45), (C-1), (C-2), (C-3), (C-4), (C-16), (C-17) and (C-23)] was charged into a stainless steel reaction tube having an inside diameter of 2.5 cm and a length of 60 cm, followed by heating to 350° C. over a metal bath. A feed gas consisting of methacrolein:$O_2$:$N_2$:$H_2O$:isobutylene = 1:1.5:17.5:9.9:0.1 (molar ratio) was passed through the catalyst layer for a contact time of 1.8 seconds (based on 0° C., 1 atmosphere) to conduct the reaction. The results obtained are shown in Table 4. The purity of the methacrolein used was 99.5% by weight.

From the results of Table 4, it is seen that even if the feed gas contains isobutylene, the catalyst of the present invention exhibits equal catalytic activity to that exhibited when the feed gas does not contain isobutylene (see Table 1-1 and Table 3-1), while the control catalyst shows a much inferior catalytic activity compared to that shown when the feed gas contains no isobutylene (see Table 1-2 and Table 3-2).

TABLE 4

| Catalyst No | Composition of catalyst (atomic ratio) | Conversion of methacrolein (%) | Per-pass yield (selectivity) of methacrylic acid (%) |
|---|---|---|---|
| Present Invention | | | |
| (1) | $Mo_{12}P_2Be_1K_2$ | 66.1 | 46.4 (70.2) |
| (5) | $Mo_{12}P_2Ag_1Rb_2$ | 69.2 | 47.6 (68.8) |
| (7) | $Mo_{12}P_2Y_1Tl_2$ | 74.5 | 52.3 (70.2) |
| (9) | $Mo_{12}P_2La_{0.5}Rb_2$ | 75.3 | 51.4 (68.3) |
| (12) | $Mo_{12}P_2Nd_{0.5}Cs_2$ | 74.5 | 48.8 (65.5) |
| (35) | $Mo_{12}P_2La_{0.2}Cs_2V_1$ | 81.1 | 60.0 (74.0) |
| (37) | $Mo_{12}P_2Nd_{0.5}Rb_2Cr_1$ | 76.1 | 52.5 (69.0) |
| (45) | $Mo_{12}P_2La_{0.2}Tl_2Zr_1$ | 81.3 | 54.9 (67.5) |
| Control | | | |
| (C-1) | $Mo_{12}P_2K_2$ | 31.8 | 12.5 (39.3) |
| (C-2) | $Mo_{12}P_2Rb_2$ | 33.3 | 16.1 (48.3) |
| (C-3) | $Mo_{12}P_2Cs_2$ | 36.1 | 20.0 (55.4) |
| (C-4) | $Mo_{12}P_2Tl_2$ | 31.2 | 17.6 (56.4) |
| (C-16) | $Mo_{12}P_2Cs_2V_1$ | 62.0 | 39.4 (63.5) |
| (C-17) | $Mo_{12}P_2Rb_2Cr_1$ | 58.1 | 31.4 (54.0) |
| (C-23) | $Mo_{12}P_2Tl_2Zr_1$ | 54.5 | 30.4 (55.8) |

EXAMPLE 5

According to the method illustrated below, methacrylic acid was produced from isobutylene by the first stage-second stage continuous method, to examine the effects which the unreacted isobutylene or other by-products contained in the first stage oxidation reaction mixture have on the activity of the second stage oxidation catalyst.

(1) First stage oxidation catalyst

Bismuth nitrate (48.5 g), 116.5 g of cobalt nitrate, 29.1 g of nickel nitrate, 484.8 g of ferric nitrate and 10.1 g of potassium nitrate were added to 150 ml of water and dissolved with heating to make a solution (solution A). On the other hand, 212 g of ammonium molybdate was dissolved with heating in 400 ml of water, and 5.76 g of 85% phosphoric acid was further added, to form a solution (solution B). While stirring solution A with heating, solution B was added thereto, and the mixture was evaporated to dryness while stirring it thoroughly. The dry matter was dried for 8 hours at 120° C., and then calcined in a muffle furnace for 16 hours at 600° C. The resulting solid matter was pulverized and sifted to a size of 4 to 8 mesh. The product so obtained was used as the first stage oxidation catalyst, its composition being expressed as $Mo_{12}Bi_1Fe_{12}Co_4Ni_1P_{0.5}K_1$.

(2) Second stage oxidation catalyst

Each of the catalysts of the present invention [catalysts Nos. (7), (9), (12), (15), (18), (24), (31), (32), (39), and (50)] and the control catalysts [catalysts Nos. (C-1), (C-2), (C-3), (C-4), (C-12), (C-16), (C-17), (C-18) and (C-23)], both used in Examples 1 to 3, was employed as the second stage oxidation catalyst.

(3) First stage oxidation reaction 100 ml of the catalyst prepared in (1) above was packed into a stainless steel reaction tube having an inside diameter of 2.5 cm and a length of 60 cm, and heated to 340° C. using a metal bath. A feed gas in a molar ratio of isobutylene:air:steam = 4:55:41 was passed through the catalyst layer at a space velocity of 2000 hr$^{-1}$. As a result, the conversion of isobutylene was 95.5%; the per-pass yield of methacrolein, 69.4%; the selectivity of methacrolein, 72.7%; and the proportion of the unreacted isobutylene and unsaturated hydrocarbons formed as by-products contained in the reaction gas was 7.3% based on the isobutylene fed. These results of the reaction were all calculated based on carbon. Other substances formed were tarry substances solidifying below 200° C., small amounts of methacrylic acid, acetic acid, acetone, furan, diacetyl, etc., and carbon dioxide gas and carbon monoxide.

(4) Second stage oxidation reaction 100 ml of the catalyst in (2) above was packed into a stainless steel reaction tube having an inside diameter of 2.5 cm and a length of 60 cm, and heated to 350° C. using a metal bath. The reaction mixture obtained by the first stage oxidation reaction of (3) above was immediately introduced to the catalyst layer and passed therethrough. The results obtained are shown in Tables 5-1 and 5-2.

From the results of Table 5-1, it is seen that in the production of methacrylic acid from isobutylene by the first stage-second stage continuous method, the catalyst of the present invention used as the second stage oxidation catalyst, even if the unreacted isobutylene or by-products are present in the first stage oxidation reaction mixture, exhibits catalytic activity which is virtually equal to that exhibited when the unreacted isobutylene or by-products are not present in the first stage oxidation reaction mixture (see Examples 1 to 3).

On the other hand, the results of Table 5-2 show that when the control catalyst is used as the second stage oxidation catalyst, its catalytic activity is greatly lowered by the unreacted isobutylene and by-products included in the first stage oxidation reaction mixture, and hence, the control catalyst is totally unsuitable for the first stage-second stage continuous method.

TABLE 5-1

| Catalyst No. | Composition of catalyst (atomic ratio) | Conversion of methacrolein (%) | Per-pass yield (selectivity) of methacrylic acid (%) |
|---|---|---|---|
| Present Invention | | | |
| (7) | $Mo_{12}P_2Y_1Tl_2$ | 74.5 | 52.2 (70.1) |
| (9) | $Mo_{12}P_2La_{0.5}Rb_2$ | 75.0 | 50.9 (67.9) |
| (12) | $Mo_{12}P_2Nd_{0.5}Cs_2$ | 74.2 | 48.5 (65.4) |
| (15) | $Mo_{12}P_2Hf_1K_2$ | 69.5 | 47.7 (68.6) |
| (18) | $Mo_{12}P_2Be_3Cs_2$ | 67.7 | 48.0 (70.9) |
| (24) | $Mo_{12}P_4La_2Cs_2$ | 74.9 | 51.8 (69.2) |
| (31) | $Mo_{12}P_2Be_1Y_{0.5}Cs_2$ | 76.0 | 53.4 (70.3) |
| (32) | $Mo_{12}P_1La_{0.5}K_{1.5}Cs_1$ | 79.6 | 54.4 (68.3) |
| (39) | $Mo_{12}P_2Nd_{0.5}Cs_2Ba_1$ | 77.1 | 52.9 (68.6) |
| (50) | $Mo_{12}P_2Sm_{0.5}Cs_2V_{0.2}Zr_{0.5}$ | 82.2 | 61.4 (74.7) |

TABLE 5-2

| Catalyst No. | Composition of catalyst (atomic ratio) | Conversion of methacrolein (%) | Per-pass yield (selectivity) of methacrylic acid (%) |
|---|---|---|---|
| Control | | | |
| (C-1) | $Mo_{12}P_2K_2$ | 27.5 | 12.2 (44.4) |
| (C-2) | $Mo_{12}P_2Rb_2$ | 28.4 | 15.1 (53.2) |
| (C-3) | $Mo_{12}P_2Cs_2$ | 33.7 | 19.0 (56.4) |
| (C-4) | $Mo_{12}P_2Tl_2$ | 30.2 | 17.3 (57.3) |
| (C-12) | $Mo_{12}Be_1Cs_2$ | 29.1 | 7.1 (24.4) |
| (C-16) | $Mo_{12}P_2Cs_2V_1$ | 61.7 | 40.6 (65.8) |

TABLE 5-2-continued

| Catalyst No. | Composition of catalyst (atomic ratio) | Conversion of methacrolein (%) | Per-pass yield (selectivity) of methacrylic acid (%) |
|---|---|---|---|
| (C-17) | $Mo_{12}P_2Rb_2Cr_1$ | 53.6 | 30.9 (57.6) |
| (C-18) | $Mo_{12}P_2Cs_2Ba_1$ | 56.6 | 33.6 (59.4) |
| (C-23) | $Mo_{12}P_2Tl_2Zr_1$ | 53.5 | 30.5 (57.0) |

EXAMPLE 6

The oxidation reaction of acrolein was carried out under the same conditions as in Example 1, except that a gas consisting of acrolein:$O_2$:$N_2$:$H_2O$ = 1:2:8:9 (molar ratio) was used as a feed gas. The catalyst used was catalyst No. (3) of Example 1 or catalyst No. (46) of Example 3.

When catalyst No. (3) was used, the results of the reaction were an acrolein conversion of 94.7% and an acrylic acid yield of 85.4% (an acrylic acid selectivity of 90.2%). When catalyst No. (46) was used, on the other hand, the results of the reaction were an acrolein conversion of 93.5% and an acrylic acid yield of 84.1% (an acrylic acid selectivity of 89.9%).

When the same reaction was performed using as a feed gas a gas having propylene added to the above-mentioned feed gas, i.e., a gas consisting of acrolein:$O_2$:$N_2$:$H_2O$:propylene = 1:2:8:8.9:0.1 (molar ratio), either of said catalysts showed no substantial reduction in its catalytic activity, though propylene was present in the feed gas.

What we claim is:
1. A process for preparing an unsaturated carboxylic acid, which comprises catalytically oxidizing an unsaturated aldehyde selected from the group consisting of acrolein and methacrolein in the vapor phase using molecular oxygen in the presence of a catalyst expressed by the formula

$$A_a B_b C_c Mo_d P_e O_f$$

wherein A represents at least one element selected from the group consisting of K, Rb, Cs and Tl; B represents at least one element selected from the group consisting of Be, Y, La, Nd, Sm and Hf; C represents at least one element selected from the group consisting of V, Cr, Ba, Sr, Al, Sn, Pb, Mn, Zr, W and Bi; a, b, c, d, e and f are the number of atoms of A, B, C, Mo, P and O, respectively; and d is 12, a, b and e are independently 0.05 to 12, c is 0 to 12, and f is the number of oxygen atoms which satisfies the valences of the other elements.

2. The process of claim 1 wherein d is 12, a, b, c and e are independently 0.1 to 8, and f is the number of oxygen atoms which satisfies the valences of the other elements.

3. The process of claim 1 wherein the unsaturated aldehyde is acrolein.

4. The process of claim 1 wherein the unsaturated aldehyde is methacrolein.

5. The process of claim 1 wherein the reaction is carried out at a temperature of 300° to 500° C.

6. The process of claim 1 wherein the reaction is carried out in the presence of an inert gas.

* * * * *